United States Patent
Um et al.

(10) Patent No.: US 9,657,318 B2
(45) Date of Patent: May 23, 2017

(54) ELECTROCHEMICAL DETOXIFICATION METHOD OF WOOD-BASED HYDROLYSATE FOR PRODUCING BIOCHEMICALS OR BIOFUELS

(71) Applicant: Korea Institute of Science and Technology, Seoul (KR)

(72) Inventors: Youngsoon Um, Seoul (KR); Yunje Kim, Seoul (KR); Dongjin Suh, Seoul (KR); Kyung Min Lee, Seoul (KR); Jeong Myeong Ha, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 14/874,040

(22) Filed: Oct. 2, 2015

(65) Prior Publication Data

US 2016/0024535 A1 Jan. 28, 2016

Related U.S. Application Data

(63) Continuation of application No. PCT/KR2013/003749, filed on Apr. 30, 2013.

(30) Foreign Application Priority Data

Apr. 4, 2013 (KR) ........................ 10-2013-0036735

(51) Int. Cl.
| | | |
|---|---|---|
| *C12P 7/10* | (2006.01) | |
| *C12P 7/52* | (2006.01) | |
| *C12P 7/64* | (2006.01) | |
| *C12P 19/02* | (2006.01) | |
| *C12P 19/14* | (2006.01) | |
| *C12P 7/16* | (2006.01) | |

(52) U.S. Cl.
CPC ........ *C12P 7/52* (2013.01); *C12P 7/10* (2013.01); *C12P 7/16* (2013.01); *C12P 7/64* (2013.01); *C12P 19/02* (2013.01); *C12P 19/14* (2013.01); *C12P 2201/00* (2013.01); *C12P 2203/00* (2013.01); *Y02E 50/16* (2013.01); *Y02E 50/343* (2013.01)

(58) Field of Classification Search
None
See application file for complete search history.

(56) References Cited

U.S. PATENT DOCUMENTS

| 9,133,278 B2* | 9/2015 | Slupska ................ C12N 1/22 |
| 2009/0056889 A1 | 3/2009 | Ren et al. |
| 2010/0129883 A1 | 5/2010 | Eiteman et al. |
| 2011/0086395 A1 | 4/2011 | Koopman et al. |
| 2012/0309060 A1 | 12/2012 | Medoff |
| 2016/0002358 A1* | 1/2016 | Teixeira ............... C13K 13/007 435/165 |

FOREIGN PATENT DOCUMENTS

| KR | 10-0318755 B1 | 12/2001 |
| KR | 10-2009-0003967 A | 1/2009 |
| KR | 10-0879317 B1 | 1/2009 |
| KR | 10-2010-0006301 A | 1/2010 |
| KR | 10-0994594 B1 | 11/2010 |
| KR | 10-1121672 B1 | 1/2012 |
| WO | WO 2009/008616 A1 | 1/2009 |
| WO | WO 2009/137804 A1 | 11/2009 |

OTHER PUBLICATIONS

Gurram R. et al. Removal of Enzymatic and Fermentation Inhibitory Compounds from Biomass Slurries for Enhanced Biorefinery Process Efficiencies. Bioresource Technology 102(17)7850-9, Sep. 2011.*
Jeong S. et al. Improvement of the Fermentability of Oxalic Acid Hydrolysates by Detoxification Using Electrodialysis and Adsorption. Bioresource Technology 152:444-449, 2014.*
Cheng, Ke-Ke et al. "Sugarcane bagasse hemicellulose hydrolysate for ethanol production by acid recovery process." *Biochemical Engineering Journal* 38.1 (2008): 105-109. (5 pages, in English).
International Search Report issued on Aug. 27, 2013 in counterpart International Application No. PCT/KR2013/003749 (6 pages, with English translation).
Vuyyuru, Koteswara Rao, and Peter Strasser. "Oxidation of biomass derived 5-hydroxymethylfurfural using heterogeneous and electrochemical catalysis." *Catalysis Today* 195.1 (2012): 144-154. (11 page, in English).

* cited by examiner

*Primary Examiner* — Ralph Gitomer
(74) *Attorney, Agent, or Firm* — NSIP Law (57) ABSTRACT

Provided is a method for preparing a lignocellulosic biomass hydrolysate having toxicity reduced or removed and being used for fermentation by microorganisms, comprising the steps of: pretreating, hydrolyzing, and using an electrochemical detoxification method.

11 Claims, 7 Drawing Sheets

ELECTROCHEMICAL DETOXIFICATION METHOD OF WOOD-BASED HYDROLYSATE FOR PRODUCING BIOCHEMICALS OR BIOFUELS

CROSS-REFERENCE TO RELATED APPLICATION

This application claims priority to Korean Patent Application No. 10-2013-0036735, filed on Apr. 4, 2013, and to International Application No. PCT/KR2013/003749, filed on Apr. 30, 2013, and all the benefits accruing therefrom under 35 U.S.C. §119, the contents of which in its entirety are herein incorporated by reference.

TECHNICAL FIELD

The present disclosure relates to a lignocellulosic hydrolysate with reduced toxicity, a method for preparing the same, and a method for preparing a biochemical or a biofuel using the same.

BACKGROUND ART

It is expected that the future society will be a resource-cycling society. In this respect, the realization of energy production using biomass is essential. Active efforts are necessary for the development of resources and environmental technologies to cope with the depletion of fossil fuel, worldwide global warming, etc. Also, technological developments for producing energy from waste environmental resources such as biomass are being fostered. The most abundant biomass on earth is lignocellulose. Lignocellulose is a complex polymer consisting of lignin, cellulose and hemicellulose. Pretreatment is necessary because most of the microorganisms that produce bioenergy and useful chemical materials cannot utilize lignocellulose directly.

After the pretreatment process, sugars that can be utilized by the microorganisms such as glucose, xylose, etc. are generated. But, together with them, fermentation inhibitors which affect the growth of the microorganisms are also generated. The fermentation inhibitors can be largely classified into phenolic compounds and non-phenolic compounds. These toxic substances inhibit the growth of and fermentation by microorganisms, leading to decreased production efficiency of biochemicals or alcohols.

Therefore, detoxification of hydrolysates is necessary before fermentation to obtain products at a high yield. Detoxification methods for removing the inhibitors from the degradation products of lignocellulosic biomass can be largely classified into physicochemical methods and biological methods. These methods do not exhibit high removal efficiency of the fermentation inhibitors and show different removal efficiency for different fermentation inhibitors.

In order to produce bioenergy and chemical materials using microorganisms, development of a detoxification process which is economical and exhibits high efficiency is necessary.

DISCLOSURE

Technical Problem

The present disclosure is directed to removing or reducing the toxicity of fermentation inhibitors which inhibit the growth of and fermentation by microorganisms from a hydrolysate used for the fermentation at minimized processing cost.

Technical Solution

In an aspect, the present disclosure provides a method for preparing a lignocellulosic biomass hydrolysate with toxicity reduced or removed, which is used for fermentation by microorganisms, including: a pretreatment step of chemically pretreating a lignocellulosic biomass; and a hydrolysis step of hydrolyzing the pretreated biomass, and further including an electrochemical treatment step of electrochemically treating the pretreated biomass or the hydrolyzed biomass to reduce or remove the toxicity of the hydrolysate.

In an exemplary embodiment, the hydrolysate contains a phenolic or furanic compound.

In an exemplary embodiment, the phenolic compound is one or more selected from a group consisting of ferulic acid, coumaric acid, benzoic acid, syringic acid, vanillic acid, vanillin, 4-hydroxybenzoic acid, 4-hydroxybenzaldehyde and syringaldehyde.

In an exemplary embodiment, the furanic compound is one or more selected from a group consisting of furfural and 5-hydroxymethylfurfural (5-HMF).

In an exemplary embodiment, in the electrochemical treatment, the toxicity of a toxic compound contained in the pretreated biomass or the hydrolysate is reduced through an electrical reaction.

In an exemplary embodiment, in the electrochemical treatment, the toxicity of the toxic compound may be reduced by using an apparatus which artificially flows an electric current.

In an exemplary embodiment, in the electrochemical treatment, a voltage of 0.1-2 V may be applied.

In an exemplary embodiment, in the electrochemical treatment, an electrode may be used.

In an exemplary embodiment, the method may further include, before the electrochemical treatment, a step of determining an optimum voltage for oxidizing a toxic compound contained in the hydrolysate, and the determined voltage may be applied during the electrochemical treatment.

In another aspect, the present disclosure provides a method for preparing a biochemical or a biofuel, including a step of fermenting a lignocellulosic biomass hydrolysate prepared by the method for preparing a lignocellulosic biomass hydrolysate with toxicity reduced or removed.

In an exemplary embodiment, the fermentation may include adding microorganisms to the hydrolysate and culturing the same.

In the present disclosure, the microorganism may include any microorganism which utilizes sugars.

In an exemplary embodiment, the microorganism may include any microorganism which can perform fermentation by utilizing sugars and, as a result thereof, can produce a biochemical or a biofuel.

In an exemplary embodiment, the microorganism may be one or more selected from a group consisting of yeast, Lactic acid bacteria, *Clostridium*, *E. coli* and *Bacillus*.

In an exemplary embodiment, the microorganism may be a genetically engineered microorganism. Specifically, it may be a microorganism which has been genetically engineered through genetic recombination to be capable of producing hydrocarbon compounds similar to the existing fossil fuels such as gasoline, diesel, etc.

In an exemplary embodiment, the biochemical may be one or more of a fatty acid, a diol, a diene and an organic acid.

In an exemplary embodiment, the biofuel may be an alcohol such as ethanol or butanol, or a hydrocarbon compound which is similar to the existing fossil fuels in composition.

In the present disclosure, the fermentation may include inoculating E. coli, yeast, Clostridium or any other microorganism capable of producing a biofuel into the electrochemically treated hydrolysate. Different biofuels are produced from the fermentation depending on the particular microorganism that has been inoculated.

In another aspect, the present disclosure provides a lignocellulosic biomass hydrolysate, which is used for fermentation by microorganisms, the hydrolysate being a hydrolysate derived from a lignocellulosic biomass, containing 0.5 g/L or less of a phenolic compound based on the total volume of the hydrolysate, and containing 0.1 g/L or less of a furanic compound based on the total volume of the hydrolysate.

In another exemplary embodiment, the lignocellulosic biomass hydrolysate may contain 0.3 g/L or less of p-coumaric acid based on the total volume of the hydrolysate.

In another exemplary embodiment, the lignocellulosic biomass hydrolysate may contain 0.15 g/L or less of p-coumaric acid based on the total volume of the hydrolysate.

Advantageous Effects

In a detoxification method according to the present disclosure, the toxicity of compounds generated during a pretreatment process which inhibit the growth of and fermentation by microorganisms can be effectively removed. In addition, production efficiency can be increased since the additional cost in the detoxification process is minimized. As a result, a biochemical or a biofuel can be prepared more effectively from a lignocellulosic biomass.

BEST MODE

Hereinafter, the present disclosure will be described in detail.

In the present disclosure, a "biochemical" refers to any chemical substance that can be obtained from fermentation by microorganisms. In an exemplary embodiment, the biochemical refers to any chemical substance that can be obtained from a lignocellulosic biomass from fermentation by microorganisms. For example, it may include a fatty acid, a diol or a diene. Also, the biochemical may include an organic acid such as lactic acid, acetic acid, butyric acid or hexanoic acid.

A biochemical or a biofuel, which is used as alternative energy due to the concerns of depletion of fossil fuels and global warming, is prepared by fermenting a hydrolysate of a lignocellulosic biomass.

Although the composition and content of the chemical ingredients are different depending on whether it is derived from a coniferous or broadleaf tree, the particular tree from which it is derived, how old the tree is, or the like, the lignocellulosic biomass generally is a lignocellulose consisting of cellulose, hemicellulose, lignin, etc.

The cellulose is a polysaccharide consisting of glucose units linked mainly by $\beta$-1,4 bonds. Unlike amylose which is a starch in which glucose units are linked through $\alpha$-1,4 bonds and form a stabilized spiral structure, cellulose has a stabilized linear structure which is much stronger physically and chemically although they consist of the same glucose units.

The hemicellulose is a polysaccharide with a lower degree of polymerization than cellulose. It mainly consists of the pentose xylose, and also contains the pentose arabinose and hexoses such as mannose, galactose, glucose, etc. Because the hemicellulose has a lower degree of polymerization and lower structural regularity than the cellulose, it is degraded relatively easily during the pretreatment of biomass.

The lignin is a polymer with a large molecular weight and a complex structure. It has hydrophobic properties because it is formed from the polymerization of many aromatic compounds such as methoxylated coumaryl alcohol (p-coumaryl alcohol), coniferyl alcohol, sinapyl alcohol, etc. Since the lignin is highly durable naturally or chemically, it is regarded as the most hardly degradable natural compound occurring in nature.

Since the lignin is covalently linked to the hemicellulose and since the hemicellulose is linked to the cellulose via hydrogen bonding, the lignocellulose has an overall structure in which a straight cellulose microfibril is surrounded by the hemicellulose through hydrogen bonding and, in turn, the hemicellulose is surrounded by the lignin through covalent bonding.

Actually, the technical and economic difficulties in the preparation of biofuels from the lignocellulosic biomass arise from the relatively high content of lignin as compared to those of the starch or (hemi)cellulose.

The lignocellulosic biomass contains 33-51 wt % of cellulose, 19-34 wt % of hemicellulose, 21-32 wt % of lignin and 0-2 wt % ash. During the hydrolysis process, the cellulose and the hemicellulose are hydrolyzed to pentoses or hexoses including glucose, galactose, mannose, rhamnose, xylose and arabinose.

Also, non-phenolic compounds such as furan, hydroxymethylfurfural (HMF), furfural, weak acids, etc. are generated from the cellulose and the hemicellulose during the pretreatment and/or hydrolysis process(es). And, phenolic compounds such as ferulic acid, coumaric acid, benzoic acid, syringic acid, vanillic acid, vanillin, 4-hydroxybenzoic acid, 4-hydroxybenzaldehyde, syringaldehyde, etc. are generated from the lignin.

The pretreatment step of pretreating the lignocellulosic biomass may include, before hydrolyzing the polysaccharide contained in the lignocellulosic biomass into low-molecular-weight sugars that can be utilized by microorganisms, a process of softening the hard lignocellulosic biomass to make the hydrolysis easy. The pretreatment may include at least one of chemical treatment of treating with an acid, a base, etc., physical treatment of applying high temperature, high pressure, etc. and biological treatment of adding enzymes, microorganisms, etc., although not being limited thereto.

Of the compounds generated from the pretreatment or hydrolysis of the lignocellulosic biomass, the phenolic or furanic compounds, which are fermentation inhibitors, inhibit the growth of microorganisms and the preparation of biochemicals or biofuels by microorganisms.

For effective use of the lignocellulosic biomass hydrolysate, the toxicity of the phenolic compounds should be reduced. In the present disclosure, the toxicity may be reduced or removed by electrochemically treating the pretreated lignocellulosic biomass or the hydrolyzed hydrolysate. Formerly, an electrochemical method has never been used for detoxification of lignin-derived fermentation inhibitors found in the lignocellulosic hydrolysate.

The lignin-derived fermentation inhibitors contained in the pretreated lignocellulosic biomass or hydrolysate inhibit the growth of microorganisms and reduce the productivity of biochemicals or bioalcohols by disrupting the cell membrane function of the microorganisms or by breaking the electrochemical balance of the cell membrane and greatly affect the fermentation by the microorganisms.

The electrochemical treatment is not particularly limited as long as radicals can be generated by oxidizing the toxic compounds. Redox reactions are reactions involving the transfer of electrons. Oxidation is the loss of electrons and reduction is the gain of electrons. Because the present disclosure aims at removing toxicity by oxidizing the toxic compounds, the main reaction occurs at an oxidation electrode where oxidation occurs. For example, the toxic compounds may be oxidized using a potentiostat. In addition, a carbon electrode and a metal electrode may be used, and the electrodes may be a surface electrode, a wire electrode or a needle electrode in terms of shape. The electrochemical treatment may include applying a voltage of 0.01 V or greater, 0.05 V or greater, 0.1 V or greater or 0.5 V or greater. Or, a voltage of 50 V or less, 20 V or less, 10 V or less, 5 V or less or 2 V or less may be applied. For example, a voltage of 0.1-2 V may be applied. The electrochemical treatment time may be 0.1-24 hours, 1-12 hours or 2-8 hours. Within the above-described range, various phenolic or furanic compounds can be oxidized fairly well. Because different fermentation inhibitors have different optimum oxidation conditions, it is needed to apply an optimum voltage for each toxic compound. But, even when there exist more than two kinds of fermentation inhibitors, if one toxic compound is oxidized, various other fermentation inhibitors can be removed simultaneously through an action of the oxidized toxic compound. The optimum voltage for each toxic compound can be determined by cyclic voltammetry. As an example, the toxicity of coumaric acid which exhibits the highest toxicity decreases by almost 100% when electrochemically treated at an optimum voltage determined by cyclic voltammetry.

The present disclosure provides a method for preparing a biochemical or a biofuel, including a step of fermenting a lignocellulosic biomass hydrolysate with the toxicity of which has been reduced by the above-described detoxification method.

The hydrolysate contains sugars that can be utilized by microorganisms for the fermentation.

The fermentation can be achieved by biologically treating the hydrolysate with microorganisms. That is to say, the fermentation of the hydrolysate can be accomplished by the microorganisms added to the hydrolysate. The microorganisms used for the fermentation of the hydrolysate may be selected considering the productivity of carboxylic acids, resistance to carboxylic acids, resistance to fermentation inhibitors that may remain in the hydrolysate, fermentation capability for pentoses and hexoses, etc.

For example, as the microorganisms, one or more of yeast, Lactic acid bacteria, *Clostridium*, *E. coli*, *Bacillus*, etc. may be used alone or in combination, although not being particularly limited thereto. These microorganisms may produce carboxylic acids innately or be conferred with the ability of producing carboxylic acids through strain improvement, or their ability of producing carboxylic acids may be enhanced through strain improvement.

The microorganisms may be one or more selected from a group consisting of *Anaeromyxobacter* sp., *Alcaligenes* sp., *Bacteroides* sp., *Bacillus* sp., *Clostridium* sp., *Escherichia* sp., *Lactobacillus* sp., *Lactococcus* sp., *Pichia* sp., *Pseudomonas* sp., *Ralstonia* sp., *Rhodococcus* sp., *Saccharomyces* sp., *Streptomyces* sp., *Thermus* sp., *Thermotoga* sp., *Thermoanaerobacter* sp. and *Zymomonas* sp.

The microorganisms may be one or more selected from a group consisting of *Clostridium beijerinckii*, *Clostridium acetobutyricum*, *Clostridium butyricum*, *Clostridium cellulolyticum*, *Clostridium thermocellum*, *Clostridium perfingens*, *Clostridium sprorogenes*, *Clostridium thermohydrosulfuricum*, *Clostridium kluyveri*, *Clostridium aciditolerans*, *Clostridium pasteurianum*, *Clostridium ljungdahlii*, *Clostridium autoethanogenum*, *Clostridium formicoaciticum*, *Clostridium thermoaceticum*, *Clostridium aceticum* and *Clostridium tyrobutyricum*.

Different biochemicals or biofuels may be produced depending on the microorganisms used. Non-limiting examples of the biochemical may include an organic acid such as lactic acid, acetic acid, butyric acid or hexanoic acid, a fatty acid, a diol or a diene. Non-limiting examples of the biofuel may include ethanol or butanol. The biofuel may be produced using the produced organic acid.

In the present disclosure, the toxicity of phenolic compounds which act as major inhibitors during the fermentation of the pretreated lignocellulosic biomass or the hydrolysate into biofuels is reduced through the electrochemical treatment. Through this, the disadvantages of the previously known physicochemical and biological detoxification methods, i.e., complexity of the associated processes and loss of sugars, can be overcome.

The hydrolysate pretreated according to the present disclosure can be used for fermentation by any microorganism capable of producing bioalcohols, such as yeast, *Clostridium*, *E. coli*, etc., and it may be used to prepare biochemicals or biofuels.

In an exemplary embodiment, the lignocellulosic biomass hydrolysate, which is used for fermentation by microorganisms, may be a hydrolysate derived from a lignocellulosic biomass, contain a phenolic compound reduced by 50 wt % or more as compared to before electrochemical treatment, and contain a furanic compound reduced by 90 wt % or more as compared to before electrochemical treatment. The hydrolysate may contain a phenolic compound reduced by 50 wt % or more, 51 wt % or more or 52 wt % or more as compared to before electrochemical treatment. Also, the hydrolysate may contain a phenolic compound reduced by 70 wt % or more, 75 wt % or more, 80 wt % or more or 82 wt % or more as compared to before electrochemical treatment. The hydrolysate may contain a furanic compound reduced by 92 wt % or more, 94 wt % or more, 96 wt % or more, 98 wt % or more or 99 wt % or more as compared to before electrochemical treatment.

In another exemplary embodiment, the lignocellulosic biomass hydrolysate, which is used for fermentation by microorganisms, may be a hydrolysate derived from a lignocellulosic biomass and may contain p-coumaric acid reduced by 45 wt % or more as compared to before electrochemical treatment. The hydrolysate may contain p-coumaric acid reduced by 46 wt % or more, 47 wt % or more, 48 wt % or more, 49 wt % or more or 50 wt % or more as compared to before electrochemical treatment. Also, the hydrolysate may contain p-coumaric acid reduced by 60 wt % or more, 65 wt % or more, 70 wt % or more, 75 wt % or more or 78 wt % or more as compared to before electrochemical treatment.

In another exemplary embodiment, the lignocellulosic biomass hydrolysate, which is used for fermentation by microorganisms, may be a hydrolysate derived from a lignocellulosic biomass and may contain ferulic acid reduced by 25 wt % or more as compared to before electrochemical treatment. The hydrolysate may contain ferulic acid reduced by 26 wt % or more, 27 wt % or more, 28 wt % or more, 29 wt % or more or 30 wt % or more as compared to before electrochemical treatment. In another exemplary embodiment, the hydrolysate may contain ferulic acid reduced by 60 wt % or more, 65 wt % or more, 70 wt % or more, 75 wt % or more or 76 wt % or more as compared to before electrochemical treatment.

In another exemplary embodiment, the lignocellulosic biomass hydrolysate, which is used for fermentation by microorganisms, may be a hydrolysate derived from a lignocellulosic biomass and may contain vanillin reduced by 45 wt % or more as compared to before electrochemical treatment. The hydrolysate may contain vanillin reduced by 42 wt % or more, 44 wt % or more, 46 wt % or more, 48 wt % or more or 49 wt % or more as compared to before electrochemical treatment. In another exemplary embodiment, the hydrolysate may contain vanillin reduced by 70 wt % or more, 75 wt % or more, 80 wt % or more or 82 wt % or more as compared to before electrochemical treatment.

In another exemplary embodiment, the lignocellulosic biomass hydrolysate, which is used for fermentation by microorganisms, may be a hydrolysate derived from a lignocellulosic biomass and may contain syringaldehyde reduced by 70 wt % or more as compared to before electrochemical treatment. The hydrolysate may contain syringaldehyde reduced by 72 wt % or more, 74 wt % or more, 76 wt % or more or 78 wt % or more as compared to before electrochemical treatment.

In another exemplary embodiment, the hydrolysate may contain syringaldehyde reduced by 80 wt % or more, 85 wt % or more, 90 wt % or more or 94 wt % or more as compared to before electrochemical treatment.

In an exemplary embodiment, the hydrolysate may contain furfural and 5-hydroxymethylfurfural (5-HMF) reduced by 90 wt % or more respectively as compared to before electrochemical treatment.

In an exemplary embodiment, the lignocellulosic biomass hydrolysate, which is used for fermentation by microorganisms, may be a hydrolysate derived from a lignocellulosic biomass and may contain a phenolic compound in an amount of 0.5 g/L or less based on the total volume of the hydrolysate and may contain a furanic compound in an amount of 0.1 g/L or less based on the total volume of the hydrolysate. The phenolic compound may be contained in an amount of 0.4 g/L or less, 0.3 g/L or less, 0.2 g/L or less or 0.1 g/L or less based on the total volume of the hydrolysate. The furanic compound may be contained in an amount of 0.05 g/L or less, 0.01 g/L or less, 0.005 g/L or less or 0.001 g/L or less based on the total volume of the hydrolysate.

In another exemplary embodiment, the lignocellulosic biomass hydrolysate may contain p-coumaric acid in an amount of 0.3 g/L or less, 0.25 g/L or less, 0.2 g/L or less, 0.15 g/L or less, 0.14 g/L or less, 0.13 g/L or less, 0.12 g/L or less or 0.11 g/L or less based on the total volume of the hydrolysate.

In another exemplary embodiment, the lignocellulosic biomass hydrolysate may contain ferulic acid in an amount of 0.4 g/L or less based on the total volume of the hydrolysate, may contain vanillin in an amount of 0.3 g/L or less based on the total volume of the hydrolysate, and may contain syringaldehyde in an amount of 0.2 g/L or less based on the total volume of the hydrolysate.

In another exemplary embodiment, the lignocellulosic biomass hydrolysate may contain ferulic acid in an amount of 0.4 g/L or less, 0.35 g/L or less, 0.3 g/L or less, 0.25 g/L or less, 0.2 g/L or less, 0.15 g/L or less, 0.12 g/L or less or 0.11 g/L or less based on the total volume of the hydrolysate.

In another exemplary embodiment, the lignocellulosic biomass hydrolysate may contain vanillin in an amount of 0.3 g/L or less, 0.25 g/L or less, 0.2 g/L or less, 0.15 g/L or less, 0.1 g/L or less or 0.09 g/L or less based on the total volume of the hydrolysate.

In another exemplary embodiment, the lignocellulosic biomass hydrolysate may contain syringaldehyde in an amount of 0.2 g/L or less, 0.15 g/L or less, 0.1 g/L or less, 0.05 g/L or less, 0.04 g/L or less or 0.03 g/L or less based on the total volume of the hydrolysate.

In another exemplary embodiment, the lignocellulosic biomass hydrolysate may be substantially free of furfural and 5-hydroxymethylfurfural (5-HMF).

The expression "substantially free of" means that the compound is contained at a concentration which is not detectable with a commonly employed detection method, e.g., 0.001 g/L or less, 0.0001 g/L or less, 0.00001 g/L or less or 0.000001 g/L or less, or is not contained at all.

Hereinafter, the present disclosure will be described in detail through examples. However, the following examples are for illustrative purposes only and it will be apparent to those of ordinary skill in the art that the scope of the present disclosure is not limited by the examples.

Mode for Invention

[Example 1] Growth of Microorganisms and Production of Butanol and Butyric Acid Depending on Phenolic Compounds After adding each phenolic compound to a medium and conducting electrochemical treatment or not, growth of microorganisms and production of butyric acid and butanol were measured. The electrochemical treatment was conducted to reduce the fermentation inhibiting activity of phenolic compounds found in a lignocellulosic hydrolysate. Then, the toxicity of each phenolic compound on microorganisms and the reduction of the toxicity after the electrochemical treatment were measured.

Figure 1:
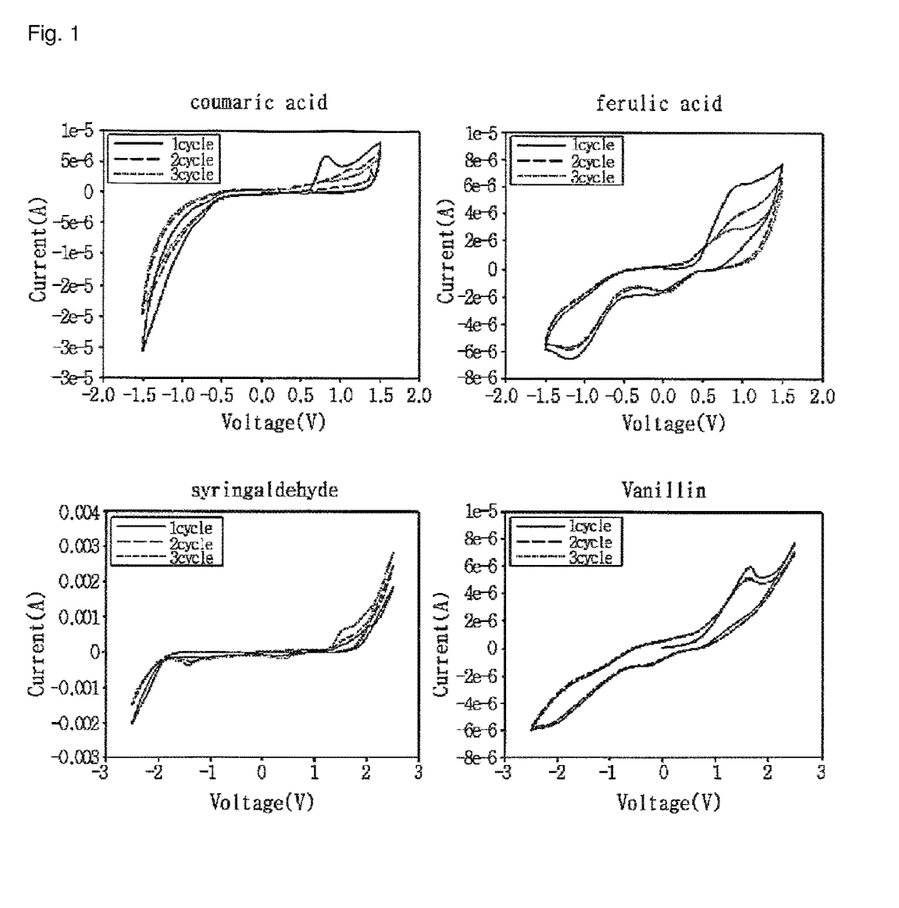
FIG. 1 shows a result of cyclic voltammetry for different phenolic compounds.

First, the optimum voltage for removing each phenolic compound through the electrochemical treatment was determined by cyclic voltammetry. The result is shown in FIG. 1. FIG. 1 shows the result of cyclic voltammetry for different phenolic compounds. In FIG. 1, the abscissa represents voltage (V) and the ordinate represents current (A). It can be seen that each phenolic compound shows an oxidation peak at an intrinsic voltage and the peak decreases gradually with the cycle number. This means that each of the phenolic compounds is removed by oxidation at the intrinsic voltage.

In order to measure the removal rate of phenolic and furanic compounds, p-coumaric acid, ferulic acid, syringaldehyde and vanillin were selected as phenolic compounds and furfural and 5-hydroxymethylfurfural were selected as furanic compounds. After adding 0.5 g/L of each of the selected 6 inhibitors to a medium, electric current was flown at each optimum oxidation voltage and then removal rate was measured.

A potentiostat (WonA Tech, WMPG 1000) was used for the electrochemical treatment of the medium. Graphite felt was used as an electrode. Specifically, the electrochemical treatment was conducted for by 5 hours at an oxidation peak voltage of each fermentation inhibitor (800 mV for coumaric acid and ferulic acid, 2 V for syringaldehyde and vanillin, 1.8 V for furfural and 5-hydroxyfurfural). Then, the fermentation inhibitors were removed using such methods as gravitational sedimentation, centrifugation, membrane separation, etc. The result is shown in the following table. The percentage of the removal rate is wt %.

TABLE 1

| | p-Coumaric acid | | Ferulic acid | | Vanillin | | Syringaldehyde | | Furfural | | HMF | |
|---|---|---|---|---|---|---|---|---|---|---|---|---|
| 1$^{st}$ treatment | Post-treatment concentration (g/L) | Removal rate (%) | Post-treatment concentration (g/L) | Removal rate (%) | Post-treatment concentration (g/L) | Removal rate (%) | Post-treatment concentration (g/L) | Removal rate (%) | Post-treatment concentration (g/L) | Removal rate (%) | Post-treatment concentration (g/L) | Removal rate (%) |
| | 0.25 | 50.0 | 0.3475 | 30.5 | 0.251 | 49.8 | 0.109 | 78.2 | 0 | 100 | 0 | 100 |
| 2$^{nd}$ treatment | Post-treatment concentration (g/L) | Removal rate (%) | Post-treatment concentration (g/L) | Removal rate (%) | Post-treatment concentration (g/L) | Removal rate (%) | Post-treatment concentration (g/L) | Removal rate (%) | Post-treatment concentration (g/L) | Removal rate (%) | Post-treatment concentration (g/L) | Removal rate (%) |
| | 0.11 | 78.0 | 0.1155 | 76.9 | 0.089 | 82.2 | 0.0265 | 94.7 | 0 | 100 | 0 | 100 |

The removal rate of each of the phenolic and furanic compounds through the electrochemical treatment is shown in the above table. After the 1st electrochemical treatment, the removal rate of coumaric acid, ferulic acid, vanillin, syringaldehyde, furfural and 5-hydroxyfurfural was 50.0, 30.5, 49.8, 78.2, 100 and 100%, respectively. After the 2nd electrochemical treatment, the removal rate of coumaric acid, ferulic acid, vanillin, syringaldehyde, furfural and 5-hydroxyfurfural was 78.0, 76.9, 82.2, 94.7, 100 and 100%, respectively. The result for the furanic compounds was not shown in the table because they do not significantly inhibit the growth of *Clostridium* used in this example. All the experiments were conducted using a medium that had been subjected to the 1st electrochemical treatment.

As a butyric acid fermentation medium, a medium containing 20 g of glucose, 5 g of yeast extract, 0.2 g of magnesium sulfate, 0.01 g of manganese sulfate, 0.01 g of ferric sulfate, 0.01 g of sodium chloride, 0.5 g of monopotassium phosphate (KH$_2$PO$_4$), 0.5 g of dipotassium phosphate (K$_2$HPO$_4$) and 2 g of ammonium acetate per 1 L of the medium was used. As a butanol fermentation medium, a medium containing 20 g of glucose, 1 g of yeast extract, 0.2 g of magnesium sulfate, 0.01 g of manganese sulfate, 0.01 g of ferric sulfate, 0.01 g of sodium chloride, 0.5 g of monopotassium phosphate (KH$_2$PO$_4$), 0.5 g of dipotassium phosphate (K$_2$HPO$_4$) and 2 g of ammonium acetate per 1 L of the medium was used. Each medium was gas-substituted with argon gas and sterilized at 121° C. for 15 minutes before the experiment.

Microorganisms were inoculated into and cultured in the medium treated by the 1st electrochemical treatment and an untreated medium, respectively. The initial pH of the medium was adjusted to 6.5 using 4 N potassium hydroxide (KOH). The microorganisms were batch cultured by adding 20 mL of the medium to a 60-mL serum bottle, inoculating the phenolic compound and the microorganisms, and then culturing the microorganisms in a shaking Incubator at 37° C. for 24 hours at a rotation speed of 150 rpm.

As the microorganisms, *Clostridium tyrobutyricum* (American Type Culture Collection, ATCC 25755) was used for butyric acid fermentation, and *Clostridium beijerinckii* (The National Collection of Industrial, Food and Marine Bacteria, NCIMB 8052) was used for butanol fermentation. Both the microorganisms had been subcultured for 2 passages before experimentation.

After the culturing was completed, the concentrations of phenolic and furanic compounds, sugars and acetic acid were measured for each culture. The concentration was analyzed by liquid chromatography (Agilent model 1200). The phenolic compounds were analyzed using a diode array detector and a Zorbax eclipse XDB-C18 column (150×4.6 mm, 3.5 μm). The sugars and acetic acid were analyzed using a refractive index detector and an Aminex HPX-87H column (300×7.8 mm). The growth of the microorganisms was analyzed by measuring absorbance at 600 nm with a spectrophotometer (UVmini-1240, Shimadzu). The concentration of butyric acid and butanol was analyzed using a gas chromatography system (Agilent technology 6890N Network GC system) equipped with a flame ionized detector and an HP-INNOWax column (30 m×250 μm×0.25 μm, Agilent Technologies). The result is shown in FIGS. 2, 3, 4 and 5.

Figure 2:
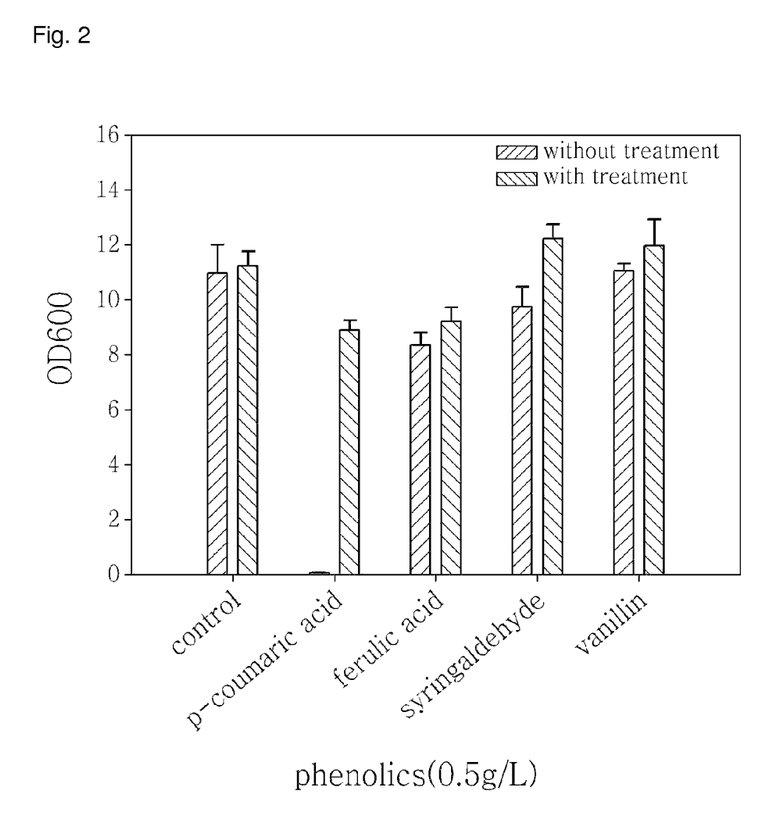
FIG. 2 and FIG. 3 show the cellular growth of Clostridium tyrobutyricum and the production of butyric acid in a medium containing 0.5 g/L of each phenolic compound before and after electrochemical treatment.
Figure 3:
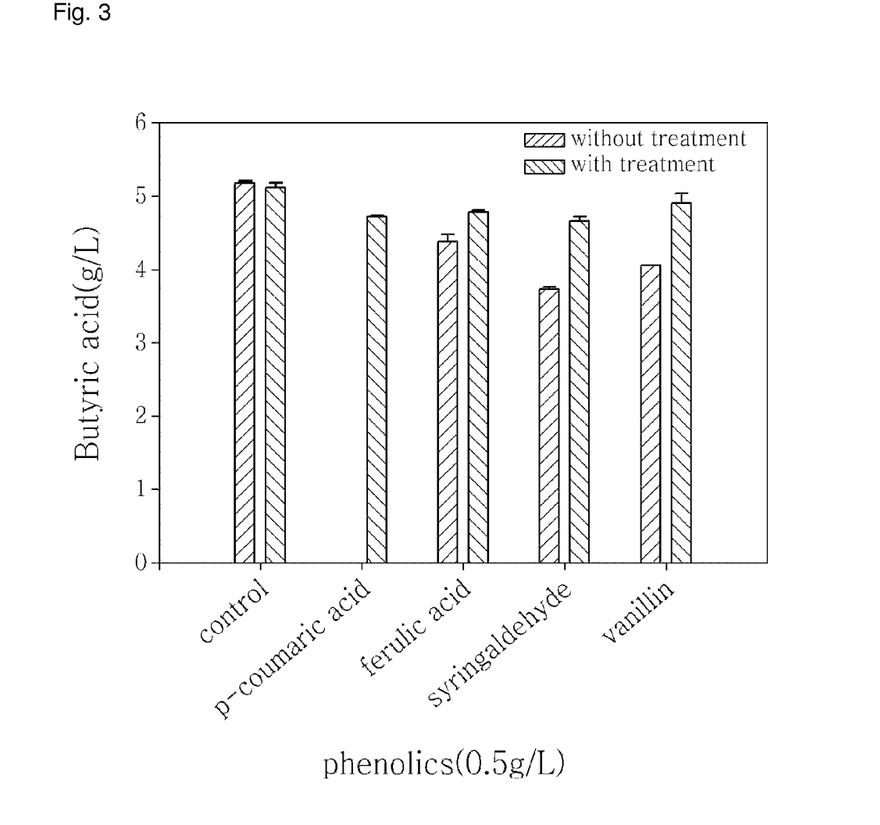

FIGS. 2 and 3 show the result of fermentation using *Clostridium tyrobutyricum* (American Type Culture Collection, ATCC 25755). Specifically, FIG. 2 shows the result of inoculating and culturing *Clostridium tyrobutyricum* and measuring the amount of the microorganisms by measuring absorbance. From FIG. 2, it can be seen that the phenolic compounds inhibit the growth of the microorganisms and the inhibition of the growth of the microorganisms by the phenolic compounds is reduced by the electrochemical treatment. Also, from the production of butyric acid by *Clostridium tyrobutyricum* in FIG. 3, it can be seen that the inhibition of the growth of the microorganisms by the phenolic compounds is reduced by the electrochemical treatment. In particular, it can be seen that although coumaric acid is a potent fermentation inhibitor which inhibits the growth of the microorganisms almost 100%, as shown in FIG. 2, its toxicity is reduced by almost 100% by the electrochemical treatment, as shown in FIG. 3.

Figure 4:
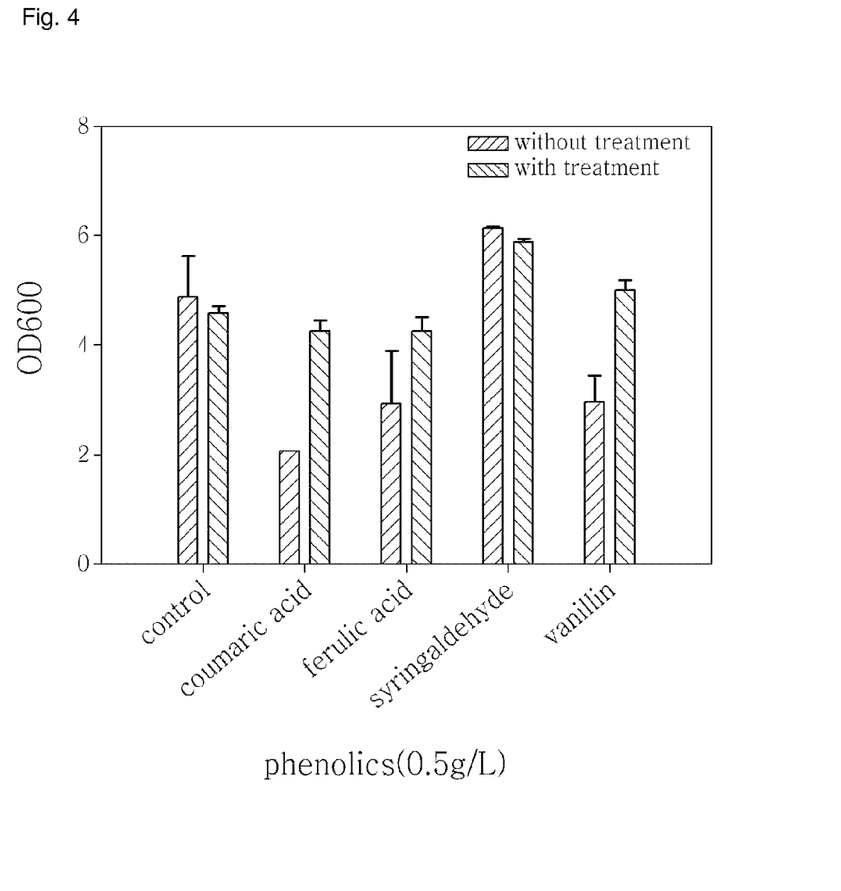
FIG. 4 and FIG. 5 show the cellular growth of Clostridium beijerinckii and the production of butanol in a medium containing 0.5 g/L of each phenolic compound before and after electrochemical treatment.
Figure 5:
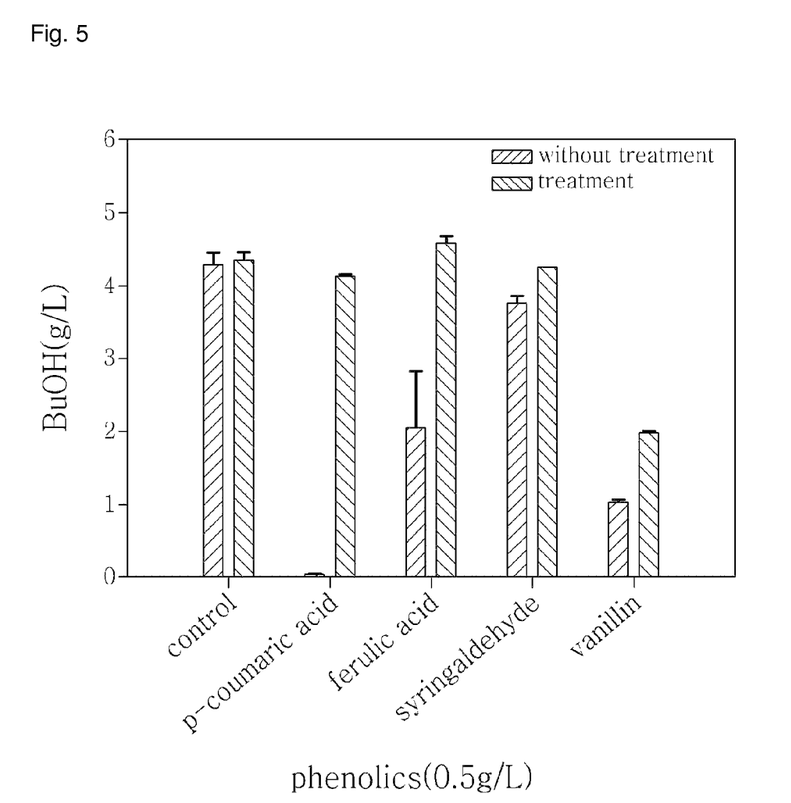

FIG. 4 and FIG. 5 show the result of fermentation using *Clostridium beijerinckii* (The National Collection of Industrial, Food and Marine Bacteria, NCIMB 8052). Specifically, FIG. 4 shows the result of inoculating and culturing *Clostridium beijerinckii* and measuring the amount of the microorganisms by measuring absorbance. From FIG. 4, it can be seen that the phenolic compounds inhibit the growth of the microorganisms and the inhibition of the growth of the microorganisms by the phenolic compounds is significantly reduced by the electrochemical treatment. Also, from the fact that the production of butanol by *Clostridium beijerinckii* is significantly increased as shown in FIG. 5, it can be seen that the toxicity by the phenolic compounds has been reduced remarkably. In particular, it can be seen the decrease in butanol production due to the toxicity of coumaric acid is recovered nearly 100% by the electrochemical treatment, as shown in FIG. 5.

[Example 2] Growth of Microorganisms and Production of Butyric Acid and Butanol after Removal of Toxic Compounds from Lignocellulose Hydrolysate Through Electrochemical Detoxification A lignocellulosic biomass hydrolysate used in this example contained 20 g/L of glucose, 5 g/L of xylose and mannose and 1.03 g/L of total phenolic compounds generated during pretreatment, as lignin-derived fermentation inhibitors.

The hydrolysate was treated with a voltage of 2 V for 5 hours and then filtered through a 0.45-μm filter. After adding the fermentation medium described above to the filtered hydrolysate, followed by sterilization, fermentation of butyric acid and butanol was conducted.

Figure 6:
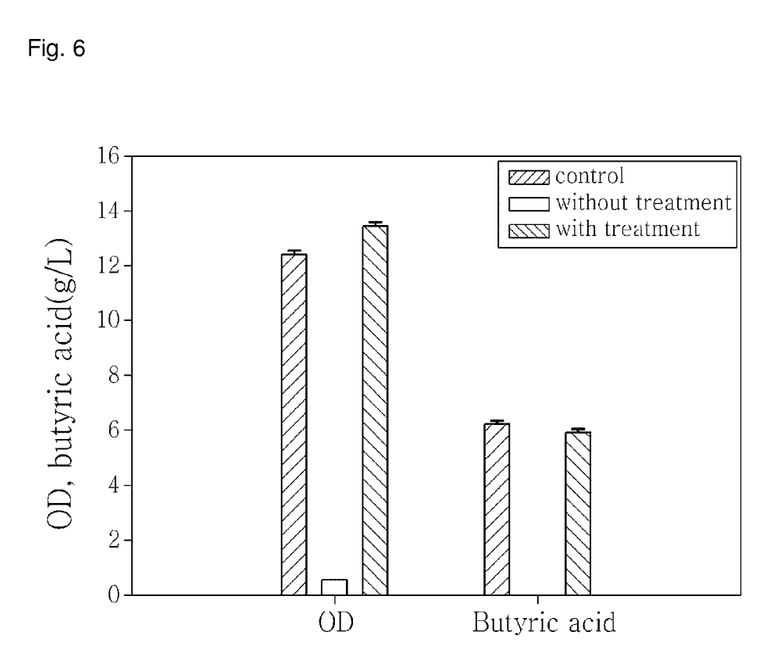
FIG. 6 and FIG. 7 show the cellular growth of Clostridium tyrobutyricum and Clostridium beijerinckii and the production of butyric acid and butanol for a hydrolysate before and after electrochemical treatment.
Figure 7:
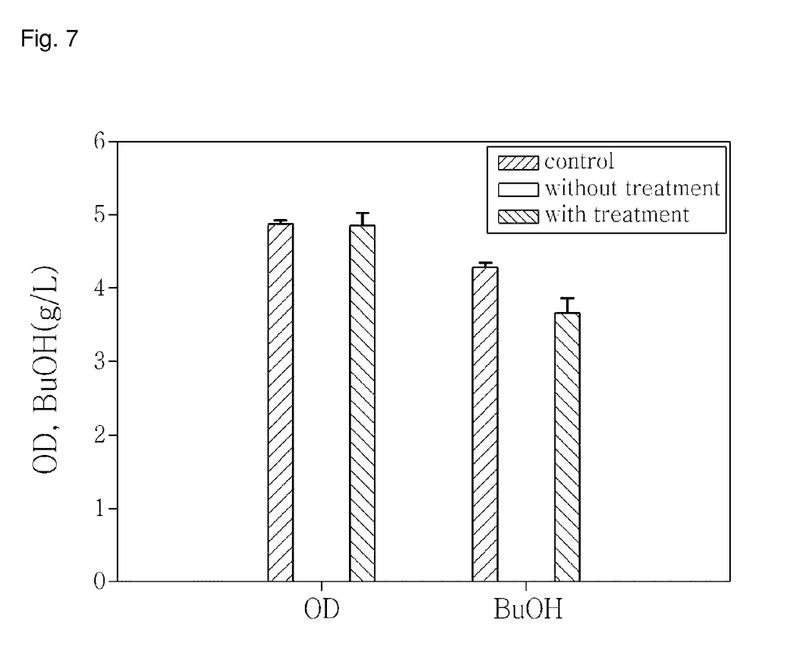

The result is shown in FIG. 6 and FIG. 7. From FIG. 6 and FIG. 7, it can be seen that although *Clostridium tyrobutyricum* and *Clostridium beijerinckii* do not grow at all in the hydrolysate, the growth of the microorganisms and the production of butyric acid and butanol increase significantly in the electrochemically treated sample.

The invention claimed is:

1. A method for preparing a lignocellulosic biomass hydrolysate, the lignocellulosic biomass hydrolysate having toxicity reduced or removed and being used for fermentation by microorganisms,
   wherein the method comprises:
   pretreating a lignocellulosic biomass; and
   hydrolyzing the pretreated biomass, and
   wherein the method further comprises electrochemically treating the pretreated biomass or the hydrolyzed biomass to generate radicals by oxidizing toxic compounds, thereby reducing or removing the toxicity of the hydrolysate, and
   wherein the resulting lignocellulosic biomass hydrolysate comprises a phenolic compound reduced by 50 wt % or more as compared to before electrochemical treatment, and comprising a furanic compound reduced by 90 wt % or more as compared to before electrochemical treatment.

2. The method for preparing a lignocellulosic biomass hydrolysate with toxicity reduced or removed according to claim 1, wherein the phenolic compound is one or more selected from a group consisting of ferulic acid, coumaric acid, benzoic acid, syringic acid, vanillic acid, vanillin, 4-hydroxybenzoic acid, 4-hydroxybenzaldehyde and syringaldehyde.

3. The method for preparing a lignocellulosic biomass hydrolysate with toxicity reduced or removed according to claim 1, wherein the furanic compound is one or more selected from a group consisting of furfural and 5-hydroxymethylfurfural (5-HMF).

4. The method for preparing a lignocellulosic biomass hydrolysate with toxicity reduced or removed according to claim 1, wherein the electrochemical treatment comprises flowing an electric current.

5. The method for preparing a lignocellulosic biomass hydrolysate with toxicity reduced or removed according to claim 1, wherein the electrochemical treatment comprises applying a voltage of 0.01-50 V.

6. The method for preparing a lignocellulosic biomass hydrolysate with toxicity reduced or removed according to claim 1, which further comprises, before the electrochemical treatment, determining an optimum voltage for oxidizing a toxic compound contained in the hydrolysate, and the electrochemical treatment comprises applying the determined voltage.

7. A method for preparing a biochemical or a biofuel, comprising,
   preparing a lignocellulosic biomass hydrolysate according to claim 1, and
   fermenting the lignocellulosic biomass hydrolysate.

8. The method for preparing a biochemical or a biofuel according to claim 7, wherein the fermentation comprises adding microorganisms to the hydrolysate and culturing the added microorganisms.

9. The method for preparing a biochemical or a biofuel according to claim 8, wherein the microorganism is one or more selected from the group consisting of yeast, Lactic acid bacteria, *Clostridium*, *E. coli* and *Bacillus*.

10. The method for preparing a biochemical or a biofuel according to claim 7, wherein the biochemical is one or more of a fatty acid, a diol, a diene and an organic acid.

11. The method for preparing a biochemical or a biofuel according to claim 7, wherein the biofuel is ethanol or butanol.

* * * * *